(12) United States Patent
Gu et al.

(10) Patent No.: US 9,517,197 B1
(45) Date of Patent: Dec. 13, 2016

(54) **TOOTHPASTE COMPOSITION CONTAINING *GANODERMA LUCIDUM* COMPONENT AND PREPARATION METHOD THEREOF**

(71) Applicant: Jiangsu Daocheng Biotechnology Co., Ltd, Yancheng (CN)

(72) Inventors: Zhengguo Gu, Yancheng (CN); Yangchun Chen, Yancheng (CN); Wei Zhang, Yancheng (CN)

(73) Assignee: Jiangsu Daocheng Biotechnology Co., Ltd., Yancheng (CN)

( * ) Notice: Subject to any disclaimer, the term of this patent is extended or adjusted under 35 U.S.C. 154(b) by 0 days.

(21) Appl. No.: 15/182,600

(22) Filed: Jun. 15, 2016

(30) Foreign Application Priority Data

Dec. 15, 2015 (CN) .......................... 2015 1 0927885

(51) Int. Cl.
| | | |
|---|---|---|
| *A61P 7/04* | (2006.01) | |
| *A61K 8/99* | (2006.01) | |
| *A61Q 11/00* | (2006.01) | |
| *A61P 1/02* | (2006.01) | |
| *A61P 31/02* | (2006.01) | |
| *A61P 31/04* | (2006.01) | |
| *A61K 8/97* | (2006.01) | |
| *A61K 8/34* | (2006.01) | |
| *A61K 8/86* | (2006.01) | |
| *A61K 8/49* | (2006.01) | |
| *A61K 8/368* | (2006.01) | |
| *A61K 8/24* | (2006.01) | |
| *A61K 8/73* | (2006.01) | |
| *A61K 8/25* | (2006.01) | |
| *A61K 8/46* | (2006.01) | |
| *A61K 8/81* | (2006.01) | |

(52) U.S. Cl.
CPC ................. *A61K 8/975* (2013.01); *A61K 8/24* (2013.01); *A61K 8/25* (2013.01); *A61K 8/345* (2013.01); *A61K 8/368* (2013.01); *A61K 8/463* (2013.01); *A61K 8/49* (2013.01); *A61K 8/731* (2013.01); *A61K 8/8152* (2013.01); *A61K 8/86* (2013.01); *A61K 8/97* (2013.01); *A61Q 11/00* (2013.01); *A61K 2800/5922* (2013.01); *A61K 2800/80* (2013.01)

(58) Field of Classification Search
USPC ........................................................ 424/728
See application file for complete search history.

(56) References Cited

FOREIGN PATENT DOCUMENTS

| CN | 103893074 | * | 7/2014 | ................ A61P 7/04 |
| CN | 104188889 | * | 10/2014 | ................ A61K 8/99 |

* cited by examiner

*Primary Examiner* — Walter Webb
(74) *Attorney, Agent, or Firm* — Wayne & King LLC

(57) ABSTRACT

The present invention discloses a preparation method for toothpaste composition containing *ganoderma lucidum* component, wherein the *ganoderma lucidum* component is sporoderm-broken *ganoderma lucidum* spore, it comprises the following steps: (1) dissolve water, sorbitol, PEG-8, propylene glycol, sodium saccharine, sodium benzoate and the extract of opuntia in a toothpaste-making pot; (2) premix calcium hydrogen phosphate, hydrated silica, sodium lauryl sulfate, cellulose gum, hydroxyethyl cellulose, sporoderm-broken *ganoderma lucidum* spore, *Panax notoginseng* powder, and radix scutellariae root powder in powder tank evenly to form a mixture; (3) stir the mixture obtained in step (2) under vacuum and inhale into the toothpaste-making pot of step (1); control the vacuum degree at minus 0.098 to minus 0.1 Mpa and stir for 15 minutes; (4) inhale the essence into the toothpaste-making pot, stir for 10 minutes, and discharge. The preparation method of the present invention is of simple technique, easy operation, and high efficiency and the obtained toothpaste composition containing *ganoderma lucidum* component has good using effect.

10 Claims, No Drawings

TOOTHPASTE COMPOSITION CONTAINING *GANODERMA LUCIDUM* COMPONENT AND PREPARATION METHOD THEREOF

CROSS-REFERENCE TO RELATED APPLICATIONS

This application is a continuation of, and claims priority to, Chinese Patent Application No. 201510927885.4 with a filing date of Dec. 15, 2015. The content of the aforementioned application, including any intervening amendments thereto, is incorporated herein by reference.

TECHNICAL FIELD

The invention relates to technical field of cosmetics processing, in particular to a toothpaste composition containing *ganoderma lucidum* component and preparation method thereof.

BACKGROUND OF THE PRESENT INVENTION

*Ganoderma lucidum* spore is tiny oval germ cell from gill of *ganoderma lucidum* in growing and mature period, namely seed of *ganoderma lucidum*. Each *ganoderma lucidum* spore is a living body with double-sporoderm structure and only 4~6 micrometer, *ganoderma lucidum* spore is surrounded by tough chitin fiber, so human bodies are hard to absorb fully, it is more suitable for intestines and stomach of human bodies to absorb directly after breaking sporoderm, *ganoderma lucidum* spore condenses the essence of *ganoderma lucidum*, its chemical effective ingredients are 75 times of *ganoderma lucidum*.

*Ganoderma lucidum* component, namely *ganoderma lucidum* spore is adopted to make toothpaste in existing market, such as Chinese Patent CN103462877A discloses a toothpaste composition containing active composition inclusion. The toothpaste composition is compounded from necessary matrixes of toothpaste and active ingredients inclusion particles occupied 0.2%~10% of composition weight, the inclusion particles comprise: a, *ganoderma lucidum* component occupied 1%~5% of active ingredients inclusion particles weight; and b, vitamin P occupied 0.1%~10% of active ingredients inclusion particles, the vitamin P is a mixture of bioflavonoid, rutin and hesperetin with weight ratio of 10:1:1. This patent also discloses the *ganoderma lucidum* component is 2%~10% of active ingredients inclusion particles weight, the *ganoderma lucidum* component is selected from basidiomycete polyporales ganodermataceae ganoderma, the *ganoderma lucidum* component is one or more of sporoderm-broken spore, *ganoderma lucidum* spore extract, *ganoderma lucidum* extract after processing *ganoderma lucidum*, *ganoderma lucidum* powder, *ganoderma lucidum* extract and chemical active substance *ganoderma lucidum* polysaccharide after purification; vitamin P is 1%~5% of active ingredients inclusion particles weight.

In above toothpaste composition, *ganoderma lucidum* or *ganoderma lucidum* sporoderm-broken spore is used as main effectiveness of active ingredients, and for keeping the activity of *ganoderma lucidum* component, it is wrapped into particles to add into the composition and released by mechanical action of brushing teeth, besides, it is compounded with various kinds of functional components, which has targeted effect, vitamin P can help to prevent and treat bleeding gums, phytic acid or salts thereof has stain removal effect, and paeonol has anti-bacterial and anti-inflammatory effects.

However, in above technical proposal, the effect of removing tartar is not so good, and taste of users is poor. So it is necessary to develop a new toothpaste composition, and *ganoderma lucidum* spore with 98% sporoderm-broken rate is only used.

SUMMARY OF THE PRESENT INVENTION

The present invention is to solve above problems by providing a preparation method for toothpaste composition containing *ganoderma lucidum* component with simple technique, easy operation, high efficiency and good using effect.

And the technique proposal of the present invention is a preparation method for toothpaste composition containing *ganoderma lucidum* component, wherein the *ganoderma lucidum* component is sporoderm-broken *ganoderma lucidum* spore, it comprises the following steps:

(1) dissolve water, sorbitol, PEG-8, propylene glycol, sodium saccharine, sodium benzoate and the extract of opuntia in a toothpaste-making pot;

(2) premix calcium hydrogen phosphate, hydrated silica, sodium lauryl sulfate, cellulose gum, hydroxyethyl cellulose, sporoderm-broken *ganoderma lucidum* spore, *Panax notoginseng* powder, and radix scutellariae root powder in powder tank evenly to form a mixture;

(3) stir the mixture obtained in step (2) under vacuum and inhale into the toothpaste-making pot of step (1); control the vacuum degree at minus 0.098 to minus 0.1 Mpa and stir for 10-20 minutes;

(4) inhale the essence into the toothpaste-making pot, stir for 10-20 minutes, and discharge.

Calcium hydrogen phosphate is used as matrix to improve the content of calcium in the toothpaste composition, mechanical action in oral cavity benefits teeth to absorb the calcium in toothpaste composition; the first step of dissolving water, sorbitol, PEG-8, propylene glycol, sodium saccharine, sodium benzoate and the extract of opuntia in a toothpaste-making pot is because the extract of opuntia is acidic material, the anti-bacterial and anti-inflammatory effects will be damaged or reduced if the extract of opuntia contacts with alkaline substance in early stage, and dissolving these substances in the toothpaste-making pot is more easily mixed with other substances under vacuum condition by studies; the mode of stirring and inhaling under vacuum can enable the formed solution in step (1) to fully absorb the mixture in step (2) in proper sequence, compared with common mixing mode in the art, the product prepared by the present invention has better taste and very obvious effect of removing tartar. Besides, using *Panax notoginseng* powder, radix scutellariae root powder cooperatively with the extract of opuntia can prevent bleeding gums.

The preferred proposal is that the parts by weight of each composition added in step (1) are: 30~40 parts of water, 10~20 parts of sorbitol, 0.5~1.5 parts of PEG-8, 0.5~1.5 parts of propylene glycol, 0.1~0.5 parts of sodium saccharine, 0.3~0.8 parts of sodium benzoate and 0.1~0.5 parts of the extract of opuntia.

The preferred proposal is that the parts by weight of each composition added in step (2) are: 40~65 parts of calcium hydrogen phosphate, 0.5~1.5 parts of hydrated silica, 0.5~1.5 parts of sodium lauryl sulfate, 0.3~0.8 parts of cellulose gum, 0.1~0.5 parts of hydroxyethyl cellulose, 0.1~0.5 parts of sporoderm-broken *ganoderma lucidum* spore, 0.1~0.5 parts of *Panax notoginseng* powder and 0.1~0.5 parts of radix scutellariae root powder.

The preferred proposal is that the parts by weight of each composition added in step (1) are: 33.5 parts of water, 10 parts of sorbitol, 1 part of PEG-8, 1 part of propylene glycol, 0.2 parts of sodium saccharine, 0.5 parts of sodium benzoate and 0.2 parts of the extract of opuntia; and the parts by weight of each composition added in step (2) are: 50 parts of calcium hydrogen phosphate, 1 part of hydrated silica, 1 part of sodium lauryl sulfate, 0.5 parts of cellulose gum, 0.1 parts of hydroxyethyl cellulose, 0.1 parts of sporoderm-broken *ganoderma lucidum* spore, 0.2 parts of *Panax notoginseng* powder and 0.2 parts of radix scutellariae root powder.

The toothpaste composition obtained by above weight ratio has the best effect of removing tartar and best taste, besides, the absorption capability of teeth to calcium is also the best after extended periods of use.

The preferred proposal is to stir for 15 minutes in step (3) and stir for 10 minutes in step (4).

In step (3) and (4), stirring time should not be too long or too short, the bubble will be generated and color is poor if stirring too long, and the mixing is insufficient if stirring too short, especially in step (3), too long stirring time will lead the caking of materials.

The preferred proposal is to carry out modified grafting to sporoderm-broken *ganoderma lucidum* spore before step (2), the modified grafting process is to carry out grafting reaction between sporoderm-broken *ganoderma lucidum* spore and starch in water and alcohol under the existence of grafting agent, wherein the weight ratio of water, alcohol, sporoderm-broken *ganoderma lucidum* spore and starch is 1:1:3:1~4, processing temperature is 35~55 DEG C and stirring time is 2~3 h, so that the modified sporoderm-broken *ganoderma lucidum* spore is obtained.

To ensure the stability of sporoderm-broken *ganoderma lucidum* spore efficacy, existing method is to cover the sporoderm-broken *ganoderma lucidum* spore with various modes and release the inner *ganoderma lucidum* powder from smashing the cover shell by mechanical effect of brushing teeth, but the preparation of this mode is rather difficult, and it cannot be ensured that sporoderm-broken *ganoderma lucidum* spore can be covered at high proportion. The present invention is to carry out modified grafting to sporoderm-broken *ganoderma lucidum* spore by changing existing method, so that the sporoderm-broken *ganoderma lucidum* spore is of independence, stable performance and better using effect.

The preferred proposal is that the grafting agent in modified grafting process is acrylate epoxy resin, and the usage amount is 5%~10% of total volume.

The preferred proposal is that the usage amount of the grafting agent in modified grafting process is 8% of total volume.

The present invention also provides a toothpaste composition containing *ganoderma lucidum* component, comprising following compositions in parts by weight: 30~40 parts of water, 10~20 parts of sorbitol, 0.5~1.5 parts of PEG-8, 0.5~1.5 parts of propylene glycol, 0.1~0.5 parts of sodium saccharine, 0.3~0.8 parts of sodium benzoate, 0.1~0.5 parts of the extract of opuntia, 40~65 parts of calcium hydrogen phosphate, 0.5~1.5 parts of hydrated silica, 0.5~1.5 parts of sodium lauryl sulfate, 0.3~0.8 parts of cellulose gum, 0.1~0.5 parts of hydroxyethyl cellulose, 0.1~0.5 parts of sporoderm-broken *ganoderma lucidum* spore, 0.1~0.5 parts of *Panax notoginseng* powder and 0.1~0.5 parts of radix scutellariae root powder.

The preferred proposal is that it comprises following compositions in parts by weight: 33.5 parts of water, 10 parts of sorbitol, 1 part of PEG-8, 1 part of propylene glycol, 0.2 parts of sodium saccharine, 0.5 parts of sodium benzoate, 0.2 parts of the extract of opuntia, 50 parts of calcium hydrogen phosphate, 1 part of hydrated silica, 1 part of sodium lauryl sulfate, 0.5 parts of cellulose gum, 0.1 parts of hydroxyethyl cellulose, 0.1 parts of sporoderm-broken *ganoderma lucidum* spore, 0.2 parts of *Panax notoginseng* powder and 0.2 parts of radix scutellariae root powder.

Wherein modified grafting is carried out to sporoderm-broken *ganoderma*, the modified grafting process is to carry out grafting reaction between sporoderm-broken *ganoderma lucidum* spore and starch in water and alcohol under the existence grafting agent, wherein the weight ratio of water, alcohol, sporoderm-broken *ganoderma lucidum* spore and starch is 1:1:3:1~4, processing temperature is 35~55 DEG C and stirring time is 2~3 h, so that the modified sporoderm-broken *ganoderma lucidum* spore is obtained, grafting agent is acrylate epoxy resin, and the usage amount of the grafting agent in modified grafting process is 8% of total volume.

DETAILED DESCRIPTION OF PREFERRED EMBODIMENTS

Embodiment 1

A toothpaste composition containing *ganoderma lucidum* component, comprising following compositions in parts by weight: 33.5 parts of water, 10 parts of sorbitol, 1 part of PEG-8, 1 part of propylene glycol, 0.2 parts of sodium saccharine, 0.5 parts of sodium benzoate, 0.2 parts of the extract of opuntia, 50 parts of calcium hydrogen phosphate, 1 part of hydrated silica, 1 part of sodium lauryl sulfate, 0.5 parts of cellulose gum, 0.1 parts of hydroxyethyl cellulose, 0.1 parts of sporoderm-broken *ganoderma lucidum* spore, 0.2 parts of *Panax notoginseng* powder and 0.2 parts of radix scutellariae root powder.

The *ganoderma lucidum* component of above toothpaste composition is sporoderm-broken *ganoderma lucidum* spore, the preparation method for toothpaste composition containing *ganoderma lucidum* component comprises the following steps:

(1) dissolve water, sorbitol, PEG-8, propylene glycol, sodium saccharine, sodium benzoate and the extract of opuntia in a toothpaste-making pot;

(2) premix calcium hydrogen phosphate, hydrated silica, sodium lauryl sulfate, cellulose gum, hydroxyethyl cellulose, sporoderm-broken *ganoderma lucidum* spore, *Panax notoginseng* powder, and radix scutellariae root powder in powder tank evenly to form a mixture;

(3) stir the mixture obtained in step (2) under vacuum and inhale into the toothpaste-making pot of step (1); control the vacuum degree at minus 0.098 Mpa and stir for 15 minutes;

(4) inhale the essence into the toothpaste-making pot, stir for 10 minutes, and discharge.

Embodiment 2

The difference with embodiment 1 is that modified grafting is carried out to sporoderm-broken *ganoderma* before step (2), the modified grafting process is to carry out grafting reaction between sporoderm-*ganoderma lucidum* spore and starch in water and alcohol under the existence grafting agent, wherein the weight ratio of water, alcohol, sporoderm-broken *ganoderma* and starch is 1:1:3:2, processing temperature is 35~55 DEG C and stirring time is 2~3 h, and the modified sporoderm-broken *ganoderma lucidum* spore is obtained, wherein the grafting agent in the process of modified grafting is acrylate epoxy resin, and the usage amount of the grafting agent is 8% of total volume (the usage amount can be 5%~10% of total volume, but the effect of 8% is better). The others are the same.

Embodiment 3

A toothpaste composition containing *ganoderma lucidum* component, comprising following compositions in parts by weight: 30 parts of water, 15 parts of sorbitol, 0.5 parts of PEG-8, 1.5 part of propylene glycol, 0.5 parts of sodium saccharine, 0.3 parts of sodium benzoate, 0.5 parts of the extract of opuntia, 65 parts of calcium hydrogen phosphate, 0.5 part of hydrated silica, 0.5 parts of sodium lauryl sulfate, 0.8 parts of cellulose gum, 0.4 parts of hydroxyethyl cellulose, 0.3 parts of sporoderm-broken *ganoderma lucidum* spore, 0.1 parts of *Panax notoginseng* powder and 0.1 parts of radix scutellariae root powder.

The *ganoderma lucidum* component of above toothpaste composition is sporoderm-broken *ganoderma lucidum* spore, the preparation method for toothpaste composition containing *ganoderma lucidum* component comprises the following steps:

(1) dissolve water, sorbitol, PEG-8, propylene glycol, sodium saccharine, sodium benzoate and the extract of opuntia in a toothpaste-making pot;

(2) premix calcium hydrogen phosphate, hydrated silica, sodium lauryl sulfate, cellulose gum, hydroxyethyl cellulose, sporoderm-broken *ganoderma lucidum* spore, *Panax notoginseng* powder, and radix scutellariae root powder in powder tank evenly to form a mixture;

(3) stir the mixture obtained in step (2) under vacuum and inhale into the toothpaste-making pot of step (1); control the vacuum degree at minus 0.098 to minus 0.1 Mpa and stir for 15 minutes;

(4) inhale the essence into the toothpaste-making pot, stir for 10 minutes, and discharge.

Modified grafting is carried out to sporoderm-broken *ganoderma* before step (2), the modified grafting process is to carry out grafting reaction between sporoderm-*ganoderma lucidum* spore and starch in water and alcohol under the existence grafting agent, wherein the weight ratio of water, alcohol, sporoderm-broken *ganoderma* and starch is 1:1:3:2, processing temperature is 35~55 DEG C and stirring time is 2~3 h, and the modified sporoderm-broken *ganoderma lucidum* spore is obtained, wherein the grafting agent in the process of modified grafting is acrylate epoxy resin, and the usage amount of the grafting agent is 8% of total volume.

Embodiment 4

The difference with embodiment 3 is that a toothpaste composition containing *ganoderma lucidum* component comprises following compositions in parts by weight 40 parts of water, 20 parts of sorbitol, 1.5 parts of PEG-8, 1 part of propylene glycol, 0.5 parts of sodium saccharine, 0.8 parts of sodium benzoate, 0.3 parts of the extract of opuntia, 65 parts of calcium hydrogen phosphate, 0.5 part of hydrated silica, 1.5 parts of sodium lauryl sulfate, 0.5 parts of cellulose gum, 0.3 parts of hydroxyethyl cellulose, 0.3 parts of sporoderm-broken *ganoderma lucidum* spore, 0.3 parts of *Panax notoginseng* powder and 0.5 parts of radix scutellariae root powder. The others are the same.

Embodiment 5

A toothpaste composition containing *ganoderma lucidum* component, comprising following compositions in parts by weight: 35 parts of water, 15 parts of sorbitol, 1 part of PEG-8, 1 part of propylene glycol, 0.1 parts of sodium saccharine, 0.5 parts of sodium benzoate, 0.1 parts of the extract of opuntia, 55 parts of calcium hydrogen phosphate, 1 part of hydrated silica, 1 part of sodium lauryl sulfate, 0.5 parts of cellulose gum, 0.1 parts of hydroxyethyl cellulose, 0.1 parts of sporoderm-broken *ganoderma lucidum* spore, 0.1 parts of *Panax notoginseng* powder and 0.1 parts of radix scutellariae root powder.

The *ganoderma lucidum* component of above toothpaste composition is sporoderm-broken *ganoderma lucidum* spore, the preparation method for toothpaste composition containing *ganoderma lucidum* component comprises the following steps:

(1) dissolve water, sorbitol, PEG-8, propylene glycol, sodium saccharine, sodium benzoate and the extract of opuntia in a toothpaste-making pot;

(2) premix calcium hydrogen phosphate, hydrated silica, sodium lauryl sulfate, cellulose gum, hydroxyethyl cellulose, sporoderm-broken *ganoderma lucidum* spore, *Panax notoginseng* powder, and radix scutellariae root powder in powder tank evenly to form a mixture;

(3) stir the mixture obtained in step (2) under vacuum and inhale into the toothpaste-making pot of step (1); control the vacuum degree at minus 0.098 to minus 0.1 Mpa and stir for 15 minutes;

(4) inhale the essence into the toothpaste-making pot, stir for 10 minutes, and discharge.

Modified grafting is carried out to sporoderm-broken *ganoderma* before step (2), the modified grafting process is to carry out grafting reaction between sporoderm-*ganoderma lucidum* spore and starch in water and alcohol under the existence grafting agent, wherein the weight ratio of water, alcohol, sporoderm-broken *ganoderma* and starch is 1:1:3:4, processing temperature is 35~55 DEG C and stirring time is 2~3 h, and the modified sporoderm-broken *ganoderma lucidum* spore is obtained, wherein the grafting agent in the process of modified grafting is acrylate epoxy resin, and the usage amount of the grafting agent is 8% of total volume.

Embodiment 6

The difference with embodiment 5 is that the weight ratio of water, alcohol, sporoderm-broken *ganoderma* and starch is 1:1:3:3.

Among above modes, embodiment 2 is the most accepted by testers.

The present invention is not limited to above embodiments, variations can be made to those ordinary skilled in the art without departing from the spirits and scope of the present invention.

We claim:

1. A preparation method for toothpaste composition containing *ganoderma lucidum* component, wherein the *ganoderma lucidum* component is sporoderm-broken *ganoderma lucidum* spore, characterized in that it comprises the following steps:

(1) dissolve water, sorbitol, PEG-8, propylene glycol, sodium saccharine, sodium benzoate and the extract of opuntia in a toothpaste-making pot;

(2) premix calcium hydrogen phosphate, hydrated silica, sodium lauryl sulfate, cellulose gum, hydroxyethyl cellulose, sporoderm-broken *ganoderma lucidum* spore, *Panax notoginseng* powder, and radix scutellariae root powder in powder tank evenly to form a mixture;

(3) stir the mixture obtained in step (2) under vacuum and inhale into the toothpaste-making pot of step (1); control the vacuum degree at minus 0.098 to minus 0.1 Mpa and stir for 10-20 minutes;

(4) inhale the essence into the toothpaste-making pot, stir for 10-20 minutes, and discharge.

2. The preparation method for toothpaste composition containing *ganoderma lucidum* component according to claim 1, the parts by weight of each composition added in step (1) is: 30~40 parts of water, 10~20 parts of sorbitol, 0.5~1.5 parts of PEG-8, 0.5~1.5 parts of propylene glycol, 0.1~0.5 parts of sodium saccharine, 0.3~0.8 parts of sodium benzoate and 0.1~0.5 parts of the extract of opuntia.

3. The preparation method for toothpaste composition containing *ganoderma lucidum* component according to claim 2, the parts by weight of each composition added in step (2) is: 40~65 parts of calcium hydrogen phosphate, 0.5~1.5 parts of hydrated silica, 0.5~1.5 parts of sodium lauryl sulfate, 0.3~0.8 parts of cellulose gum, 0.1~0.5 parts of hydroxyethyl cellulose, 0.1~0.5 parts of sporoderm-broken *ganoderma lucidum* spore, 0.1~0.5 parts of *Panax notoginseng* powder and 0.1~0.5 parts of radix scutellariae root powder.

4. The preparation method for toothpaste composition containing *ganoderma lucidum* component according to claim 3, characterized in that the parts by weight of each composition added in step (1) is: 33.5 parts of water, 10 parts of sorbitol, 1 part of PEG-8, 1 part of propylene glycol, 0.2 parts of sodium saccharine, 0.5 parts of sodium benzoate and 0.2 parts of the extract of opuntia; and the parts by weight of each composition added in step (2) is: 50 parts of calcium hydrogen phosphate, 1 part of hydrated silica, 1 part of sodium lauryl sulfate, 0.5 parts of cellulose gum, 0.1 parts of hydroxyethyl cellulose, 0.1 parts of sporoderm-broken *ganoderma lucidum* spore, 0.2 parts of *Panax notoginseng* powder and 0.2 parts of radix scutellariae root powder.

5. The preparation method for toothpaste composition containing *ganoderma lucidum* component according to claim 4, characterized in that stir for 15 minutes in step (3) and stir for 10 minutes in step (4).

6. The preparation method for toothpaste composition containing *ganoderma lucidum* component according to claim 1, characterized in that modified grafting is carried out to sporoderm-broken *ganoderma lucidum* spore before step (2), the modified grafting process is to carry out grafting reaction between sporoderm-broken *ganoderma lucidum* spore and starch in water and alcohol under the existence of grafting agent, wherein the weight ratio of water, alcohol, sporoderm-broken *ganoderma lucidum* spore and starch is 1:1:3:1~4, processing temperature is 35~55 DEG C and stirring time is 2~3 h, and the modified sporoderm-broken *ganoderma lucidum* spore is obtained.

7. The preparation method for toothpaste composition containing *ganoderma lucidum* component according to claim 6, characterized in that the grafting agent in modified grafting process is acrylate epoxy resin, and the usage amount is 5%—10% of total volume.

8. The preparation method for toothpaste composition containing *ganoderma lucidum* component according to claim 6, characterized in that the usage amount of the grafting agent in modified grafting process is 8% of total volume.

9. A toothpaste composition containing *ganoderma lucidum* component, comprising following compositions in parts by weight: 30~40 parts of water, 10~20 parts of sorbitol, 0.5~1.5 parts of PEG-8, 0.5~1.5 parts of propylene glycol, 0.1~0.5 parts of sodium saccharine, 0.3~0.8 parts of sodium benzoate, 0.1~0.5 parts of the extract of opuntia, 40~65 parts of calcium hydrogen phosphate, 0.5~1.5 parts of hydrated silica, 0.5~1.5 parts of sodium lauryl sulfate, 0.3~0.8 parts of cellulose gum, 0.1~0.5 parts of hydroxyethyl cellulose, 0.1~0.5 parts of sporoderm-broken *ganoderma lucidum* spore, 0.1~0.5 parts of *Panax notoginseng* powder and 0.1~0.5 parts of radix scutellariae root powder.

10. The toothpaste composition containing *ganoderma lucidum* component according to claim 9, characterized in that it comprises 33.5 parts of water, 10 parts of sorbitol, 1 part of PEG-8, 1 part of propylene glycol, 0.2 parts of sodium saccharine, 0.5 parts of sodium benzoate, 0.2 parts of the extract of opuntia, 50 parts of calcium hydrogen phosphate, 1 part of hydrated silica, 1 part of sodium lauryl sulfate, 0.5 parts of cellulose gum, 0.1 parts of hydroxyethyl cellulose, 0.1 parts of sporoderm-broken *ganoderma lucidum* spore, 0.2 parts of *Panax notoginseng* powder and 0.2 parts of radix scutellariae root powder.

\* \* \* \* \*